United States Patent [19]
Tam

[11] Patent Number: 5,390,111
[45] Date of Patent: Feb. 14, 1995

[54] METHOD AND SYSTEM FOR PROCESSING CONE BEAM DATA FOR RECONSTRUCTING FREE OF BOUNDARY-INDUCED ARTIFACTS A THREE DIMENSIONAL COMPUTERIZED TOMOGRAPHY IMAGE

[75] Inventor: Kwok C. Tam, Schenectady, N.Y.

[73] Assignee: General Electric Company, Schenectady, N.Y.

[21] Appl. No.: 150,901

[22] Filed: Nov. 12, 1993

[51] Int. Cl.6 .............................................. G06F 15/42
[52] U.S. Cl. ............................ 364/413.14; 364/413.16
[58] Field of Search ....................... 364/413.15, 413.14, 364/413.22, 413.16; 378/4, 20, 12

[56] References Cited

U.S. PATENT DOCUMENTS 5,187,659  2/1993  Eberhard et al. ............... 364/413.15
5,257,183  10/1993  Tam ................................ 264/413.19

Primary Examiner—Donald E. McElheny, Jr.
Attorney, Agent, or Firm—Enrique J. Mora; Paul R. Webb, II

[57] ABSTRACT

Techniques and system for processing cone beam projection data for reconstructing substantially free of boundary-induced artifacts a three-dimensional computerized tomography (CT) image of a portion of an object are provided. Such techniques include suitably identifying a rotation center shared by a line of integration pair and wherein the rotation center is selected for mapping, within a cone beam masked region identified on a surface array detector, predetermined points situated along the line of integration pair. The suitably identified rotation center allows to acquire cone beam projection data within the masked region which is free of boundary effects. The acquired data is retained for subsequent processing and thus allows for exactly reconstructing the substantially free of boundary-induced artifacts CT image.

18 Claims, 7 Drawing Sheets

METHOD AND SYSTEM FOR PROCESSING CONE BEAM DATA FOR RECONSTRUCTING FREE OF BOUNDARY-INDUCED ARTIFACTS A THREE DIMENSIONAL COMPUTERIZED TOMOGRAPHY IMAGE

CROSS REFERENCE TO RELATED APPLICATIONS

This application is related to the following commonly assigned U.S. patent applications, the entire disclosures of which are hereby expressly incorporated by reference:

Application Ser. No. 07/725,142 by Kwok C. Tam entitled "METHOD AND APPARATUS FOR ACQUIRING COMPLETE RADON DATA FOR EXACTLY RECONSTRUCTING A THREE DIMENSIONAL COMPUTERIZED TOMOGRAPHY IMAGE OF A PORTION OF AN OBJECT IRRADIATED BY A CONE BEAM SOURCE"; and Application Ser. No. 07/908,114 by Kwok C. Tam entitled "METHOD AND APPARATUS FOR PRE-PROCESSING CONE BEAM PROJECTION DATA FOR EXACT THREE DIMENSIONAL COMPUTER TOMOGRAPHIC IMAGE RECONSTRUCTION OF A PORTION OF AN OBJECT".

Application Ser. No. 08/137,543 by Kwok C. Tam entitled "METHOD AND SYSTEM FOR PRE-PROCESSING CONE BEAM DATA FOR RECONSTRUCTING FREE OF INTERPOLATION-INDUCED ARTIFACTS A THREE DIMENSIONAL COMPUTERIZED TOMOGRAPHY IMAGE".

BACKGROUND OF THE INVENTION

The present invention relates generally to three-dimensional (3D) computerized tomography (CT) and, more particularly, the present invention relates to a method and system for processing cone beam projection data for reconstructing substantially free of boundary-induced artifacts a 3D image of a portion of an object.

Commonly assigned U.S. patent application Ser. No. 07/725,142 by Kwok C. Tam discloses method and apparatus for imaging a portion of an object irradiated in a field of view of a cone beam source such as a cone beam x-ray source or other suitable point source of radiant or electromagnetic energy. A portion of interest undergoing imaging inspection may be a preselected portion of an object which is wholly engulfed within the field of view of the cone beam source. Alternatively, the portion of interest to be imaged may be limited to only that portion of the object which fits within the field of view of the cone beam source, as is typically the case when the entire object is too large to be wholly irradiated thereby. In either case, the portion of interest can be rotationally scanned by the x-ray cone beam source at respective upper and lower extents thereof along a scan trajectory having upper and lower scan paths which serve to bound the portion of interest. To ensure that a complete Radon data set is acquired for exact image reconstruction, the upper and lower scan paths are connected by a connecting scan path to effectively provide a complete scan trajectory. Cone beam projection data is detected by a suitable surface array radiation detector wherein the source and array detector are mutually fixed with respect to one another so as to scan the portion of interest to acquire cone beam projection data for a plurality of source positions along the scan trajectory.

To insure exact image reconstruction, cone beam projection data is generally acquired using a technique which fills Radon space over a region of support in Radon space corresponding to the field of view occupied by the portion of interest of the object in real space. Such filling technique is chosen to provide sufficient Radon data to completely and exactly reconstruct a 3D CT image by a process of inverse Radon transformation. Preferably, at least a requisite core number of necessary data points in Radon space can be selectively retained for subsequent processing so as to exactly image the portion of interest. A 3D CT cone beam reconstructed image obtained by inverse Radon transformation utilizes a mathematical point by point inversion technique. The Radon inversion technique is inherently a computationally intensive technique which becomes unduly burdened by tracking Radon data points which either do not contribute or redundantly contribute to reconstruction of a 3D image of the portion of interest. Typically, either each Radon data point collected throughout Radon space is indiscriminately retained for point by point inversion processing, or a truncated subset of Radon data points, representing only cone beams which actually pass through the object, is selectively retained for point by point inversion processing. Truncation boundaries in Radon space are typically identified by the use of a projection and/or intersection operations which are easier to apply than direct point by point mathematical manipulations.

In a typical 3D CT reconstruction by Radon inversion, suitable integrals such as planar integrals are calculated and organized as discrete data points in Radon space. The planar integrals are based upon cone beam projection data measured by the detector. Radon data points are organized onto an arbitrary set of planes in Radon space, wherein each plane of integration is used to calculate a Radon derivative corresponding to a single data point in Radon space. These discretely organized Radon data points are typically partitioned and selectively retained or discarded according to whether or not corresponding planes of integration intersect the portion of interest of the object. By its mathematical nature, Radon space is a collection of discrete Radon data points each corresponding to a plane of integration, e.g., a planar integral. For each integration plane that intersects the portion of interest, the corresponding computation of a Radon derivative, i.e., a Radon data point, depends upon the manner in which that plane intersects with the portion of interest. Thus, the adequacy of filling the region of support in Radon space is generally assessed by first suitably partitioning those integration planes which contribute to data points in Radon space.

Typical image reconstruction of the portion of interest generally requires the following procedure: 1) identifying a plurality of suitable integration planes; 2) determining an appropriate angular range of the x-ray cone beam for each contributing source position required to compute the Radon derivative for each identified integration plane; and 3) keeping track of the exact number of source positions that contribute to a particular Radon data point. Commonly assigned U.S. patent application Ser. No. 07/908,114 by Kwok C. Tam improves the general approach of U.S. patent application Ser. No. 07/725,142 by pre-processing cone beam projection data for image reconstruction in a manner whereby only cone beam projection data acquired within a select region identified on the surface array detector is retained for further processing. Thus, image processing using the foregoing pre-processing conveniently requires fewer operations resulting in saving time, money and computer resources.

The approach of patent application Ser. No. 07/908,114 is illustrated in FIGS. 1a and 1b. FIG. 1a illustrates an object 22 wherein a cylindrical portion 23, for example, is the portion of interest undergoing inspection. This portion is labelled "X" and is bounded by an upper scan path 24, labelled "$C_1$", and a lower scan path 26, labelled "$C_2$", with a predetermined connecting scan path therebetween (not shown). For the sake of illustration and not of limitation, upper and lower scan paths 24 and 26, are herein illustrated as circular paths enclosing the cylindrical portion of interest 23. By way of example, consider cone beam source 28 along upper scan path 24 at source position A, a projection of upper and lower scan paths 24 and 26 from source position A onto surface array detector 32 can be characterized by a boundary projection operator "P" operating on scan paths 24 and 26, respectively. The boundary projection operation on the upper scan path can be symbolically represented by $P(C_1)$ and such upper scan path simply projects onto surface array detector 32 as a straight line 34. Similarly, boundary projection operation $P(C_2)$ can be shown to project the lower scan path onto detector 32 as a parabolic curve 36.

As illustrated in FIGS. 1a and 1b, a closed region 44 on surface array detector 32 results upon operation of a mask projection operator M conceptually represented by a suitably identified region 38 in the square designated as M. Mask projection operator M upon operating on an overall cone beam projection 42 of the object 22 and cooperating with boundary operator P advantageously provides closed region 44 further shown in the square designated as MP(X). Thus, closed region 44 is obtained by taking the intersection of the overall cone beam projection 42 of object 22 with mask operator M (i.e., region 38) onto surface detector 32 wherein such intersection is bounded by $P(C_1)$ at straight line 34 and $P(C_2)$ at parabolic curve 36. Thus cone beam projection data can be acquired at the array detector for each position along the scan trajectory, retaining only that cone beam projection data acquired within region 38 for further processing. This manner of pre-processing data amounts to processing only data collected within region 38 which matches the cone beam projection of the object bounded between the respective similar projections of the upper and lower scan paths. Region 38 is herein referred to as a masked cone beam region.

For the sake of explanation, a given exemplary energy cone beam detected at surface array detector 32 within region 38, can represent, for example, the cone beam emitted from source scan position A, within an angle conveniently chosen to span at least the boundaries or edges defined by projection of upper scan path $C_1$, at straight line 34, and the projection of lower scan path $C_2$, at parabolic curve 36. Thus, it will be appreciated that such exemplary cone beam intersects at least certain predetermined subportion of portion of interest 23 being that the upper and lower scan paths as well as the connecting path cooperate to fully enclose portion of interest 23. Additional source scan positions can provide cone beam projections which are limited to within the masked cone beam region. In essence, such cone beam projections are obtained from cone beams which can be characterized as passing only through portion of interest 23 (labelled as X) without contamination by the rest of object 22, i.e., remaining portions of the object other than portion X. Based upon the above characterization there is no longer a need to distinguish between different categories of integration planes by partitioning those integration planes which contribute to data points in Radon space. Although such otherwise requisite partitioning procedure is therefore eliminated which results in saving time, money and computer resources, certain image artifacts unfortunately can occur.

To obtain cone beam projection data uncontaminated by the rest of object 22, it will be appreciated that cone beam projection data acquired outside region 38 is set to a zero value, i.e., individual detector elements such as pixel detectors situated outside the masked cone beam region are collectively set to have a respective value of zero. In particular, whenever a line of integration intersects the boundary defined by parabolic curve 36 (i.e., the lower scan path projection) boundary-induced artifacts can occur. For instance, such boundary-induced artifacts typically arise because the line of integration may loose contribution of cone beam projection data from points situated outside region 38 and in particular outside parabolic curve 36. For instance lines of integration used in calculating Radon data for the portion of interest may no longer exhibit a suitable mapping relationship for points situated along such boundary intersecting lines of integration, and generally result in an image having noticeable boundary-induced artifacts. (No representation is made or intended that these referenced applications are necessarily prior art to the present application).

OBJECTS AND SUMMARY OF THE INVENTION

Accordingly, it is a general object of the present invention to provide an improved 3D CT imaging technique.

A more specific object of the present invention is to provide for imaging a portion of an object substantially free of boundary-induced artifacts.

It is another object of the present invention to provide a technique for eliminating boundary effects upon lines of integration intersecting a predetermined boundary of a region identified for retaining cone beam projection data.

It is yet another object of the present invention to provide a system for eliminating boundary effects upon lines of integration intersecting a predetermined boundary of a region identified for retaining cone beam projection data.

The foregoing and other objects and advantages of the present invention which will become more apparent from the following detailed description are realized by a method for processing cone beam projection data for reconstructing substantially free of boundary-induced artifacts a 3D image of a portion of an object using an inverse Radon transformation. A mutually spaced cone beam source and a surface array detector are provided in fixed relationship to one another. The object undergoing inspection, for example, is provided between the source and the detector such that at least the portion of the object to be imaged is irradiated by the source. Both the source and detector can be moved relative to the object for scanning about the portion to be imaged along a scan trajectory enclosing upper and lower extents of such portion by respective upper and lower scan paths preferably joined therebetween by a predetermined connecting path.

A region is identified on the surface array detector to match a cone beam projection of the object bounded between respective similar projections of the upper and lower scan paths. Cone beam projection data is detected at predetermined points situated along respective lines of integration traversing the identified region on the surface array detector. A rotation center is identified and is shared by at least a pair of such lines of integration wherein the rotation center is selected for mapping within the identified region respective ones of the points situated along such line of integration pair. By way of example and not of limitation, the rotation center is located on the surface array detector along the lower scan path projection being obtained from source positions at the upper scan path for each line of integration pair which intersects the lower scan path projection. Further, the mapping of points along each line of integration pair preferably provides a one-to-one onto mapping relationship. Cone beam data acquired within the identified region is retained for subsequent processing to reconstruct substantially free of boundary-induced artifacts a 3D image of the portion using the inverse Radon transformation. In general the rotation center can be located on the surface array detector along a predetermined one of the upper and lower scan path projections such that the one scan path projection whereon the rotation center is located is obtained from source positions located at the respective one of the upper and lower scan paths which forms the other of the upper and lower scan path projections.

The three-dimensional computerized tomography system according to the present invention includes a suitable cone beam source for irradiating at least a portion of the object to be imaged. A surface array detector is positioned to receive radiation from the source. A scanning device causes relative motion of the source and object such that the source moves along a scan trajectory relative to the portion of the object to be imaged. The scanning device includes means for scanning along upper and lower scan paths respectively enclosing upper and lower extents of the portion of the object and along a connecting path between the upper and lower scan paths. Means for identifying a region on the surface array detector allows to match a cone beam projection of the object bounded between the upper and lower scan projection paths. Means for acquiring cone beam projection data at predetermined points situated along respective lines of integration traversing the identified region cooperate to acquire complete cone beam projection data corresponding to the portion of the object to be imaged. The system further includes means for identifying a rotation center shared by at least a pair of lines of integration, as discussed above. Mean for retaining the cone beam projection data acquired within the identified region can be utilized by means for processing such retained data (such as a computer work station and the like) to construct an exact 3D image of the portion of the object substantially free of boundary-induced artifacts using the Radon inverse transformation. A display can be connected to the computer workstation for displaying such image.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

DETAILED DESCRIPTION OF THE INVENTION

Figure 1A:
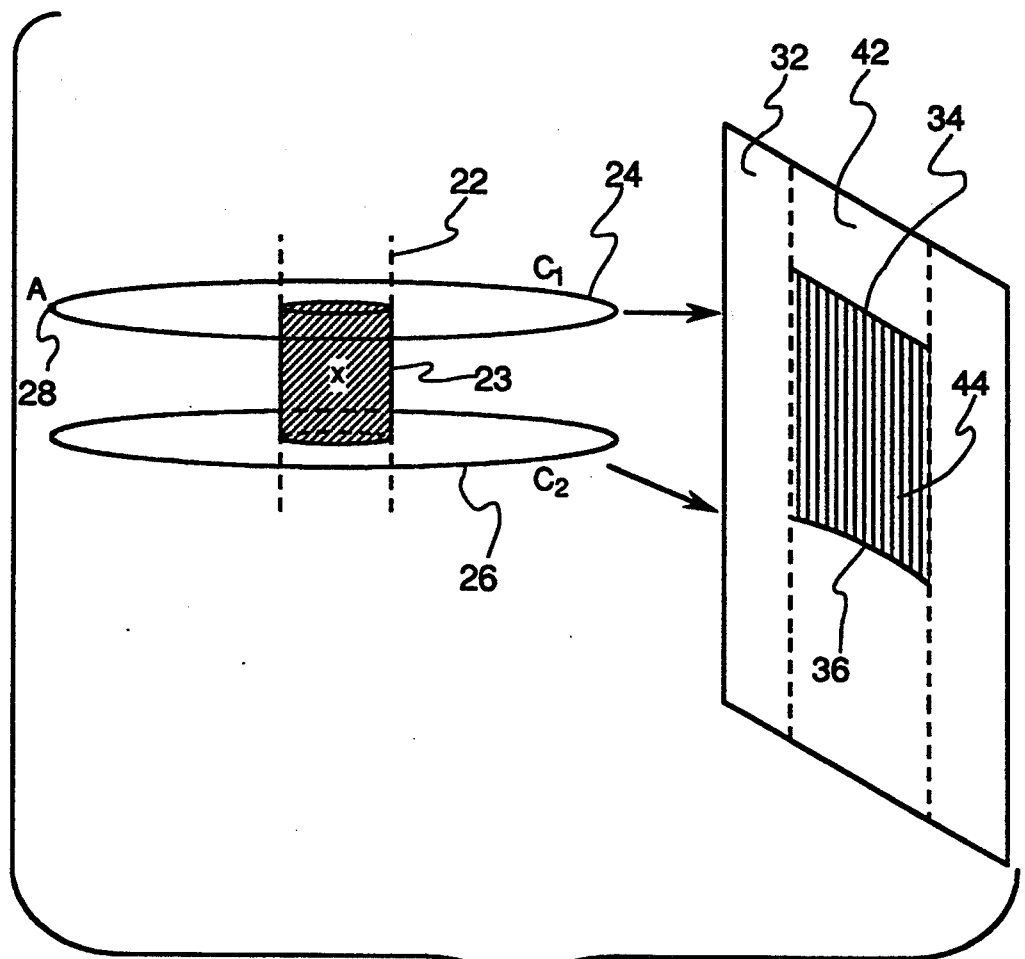
FIGS. 1a and 1b depict an exemplary configuration wherein a cone beam radiation source and a surface array detector scan a portion of an object to be imaged and wherein only data acquired within a region identified on the array detector is retained for further image processing.
Figure 1B:
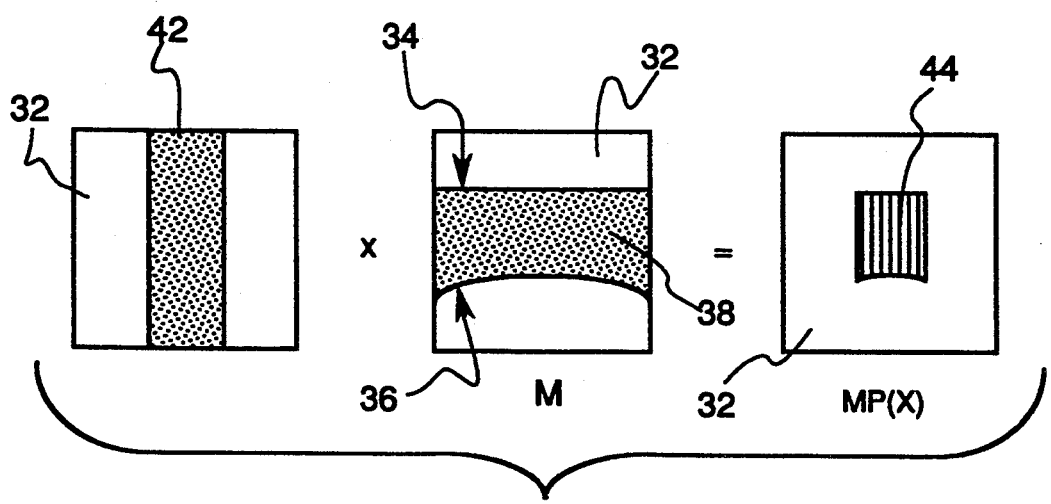

In a typical scanning and data acquisition configuration which employs cone beam geometry, as discussed in the context of FIGS. 1a and 1b in the background section of the present disclosure, the field of view of the source can enclose a portion of the object or workpiece to be imaged. More generally, it will be understood that the object is not necessarily a workpiece or a portion thereof, but may be a human or animal patient or portion thereof which is to be imaged for medical purposes. In either case, a suitable cone beam source 28 and a typical surface array detector 32 cooperate along a defined source scan trajectory in a manner generally well understood by those skilled in the art to provide cone beam projection data. Whether the object is part of a workpiece being inspected for industrial purposes, or a portion of a human or a animal patient being analyzed for medical purposes, the frame of reference which will be generally used in this discussion will be the frame of reference of the object. Thus, the discussion will refer to the trajectory or scan path of source 28. However, it will be understood that the relative motion between source 28 and the object may be accomplished by: moving source 28 while the object remains stationary, moving the object while source 28 is stationary, or by moving both the object and source 28 at the same time. In medical applications where the object is a patient or part of a patient, source 28 is usually moved while the patient is stationary. In industrial applications where the object may be part or all of a workpiece, the workpiece is usually moved while the source 28 is maintained stationary.

As is generally appreciated in the field of three-dimensional computerized tomography (CT), surface array detector 32 which can be conveniently implemented as a planar surface array detector detects cone beam radiation which has passed through at least a portion of the object to be imaged. Usually, and as contemplated by the present invention, the array detector would be fixed relative to source 28, that is, the detector would move relative to the object, but not relative to the source 28. However, the present invention does not necessarily require that the area detector is fixed relative to source 28. The source 28 is preferably an x-ray cone beam radiation source, but could be alternatively a source of neutrons, positrons, or other form of radiation or electromagnetic energy from a point source.

Figure 2:
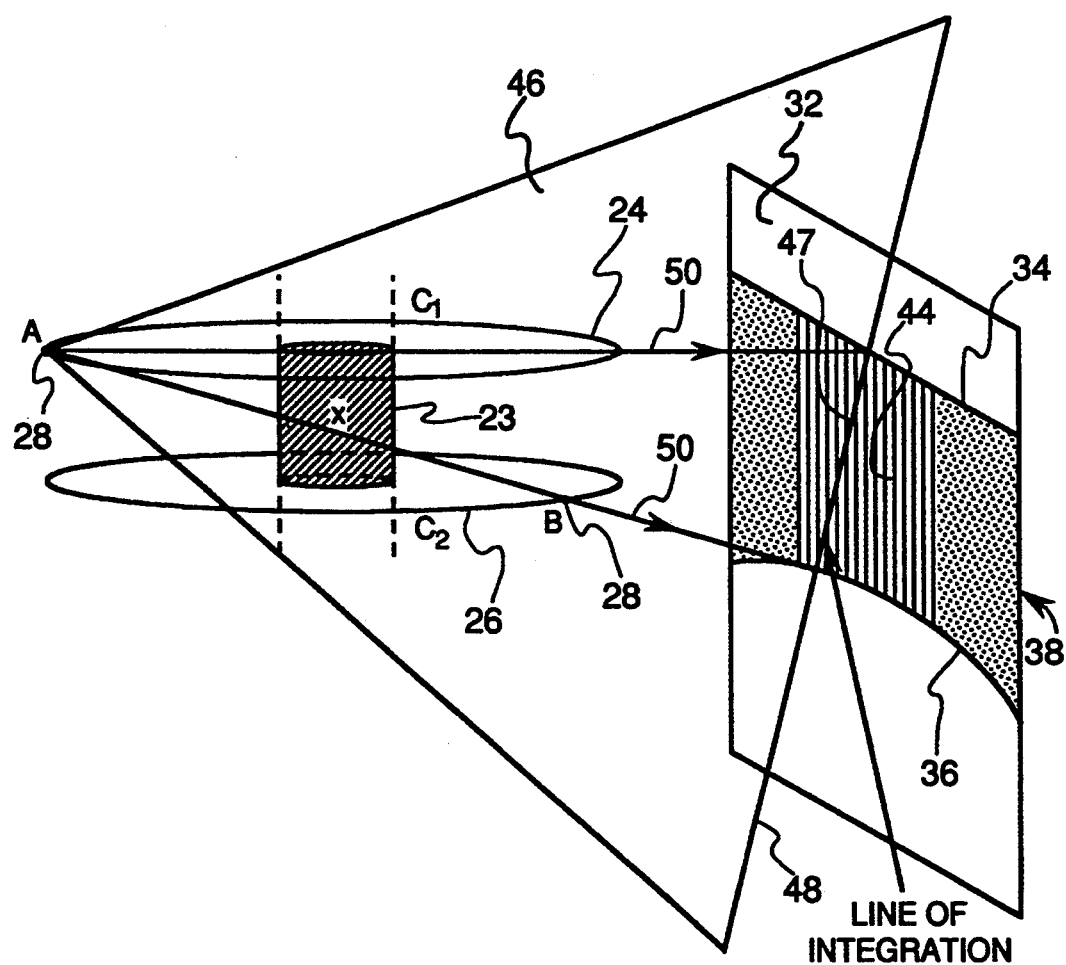
FIG. 2 depicts an exemplary plane for conceptually illustrating a line of integration for obtaining Radon data.

FIG. 2 illustrates that any plane, such as exemplary plane 46, which intersects a given source scan position A, for example, and portion of interest 23, also intersects surface array detector array 32 along a line 48 which extends through region 38, i.e., the masked cone beam region. The segment of line 48 identified by numeral 47 lying within region 38, corresponds to x-ray beams emitted from source position A within an angle conveniently chosen to span upper scan path projection 24 and lower scan path projection 26, as previously illustrated in FIG. 1a. This angular range is precisely the same angular range of cone beam data needed to compute a Radon derivative for at least an upper subportion of portion X, such as the upper subportion spanned by exemplary rays 50. Thus, utilizing cone beam data acquired within region 38, conveniently provides the Radon derivative for at least such upper subportion of portion X. Similarly, source position B can be shown to provide the Radon derivative corresponding to the remaining lower subportion of portion X. Although line segment 47 is shown in FIG. 2 as traversing region 38 in a generally vertical direction, such line segment could have been shown as traversing region 38 in a horizontal direction generally parallel to scan path projections 34 and 36. In each case, line segment 47 can conceptually represent a line of integration upon which a suitable integration operation, such as for example a predetermined weighted integration operation, is performed to acquire Radon data which corresponds to the point in Radon space for which the Radon derivative is being calculated.

Figure 3:
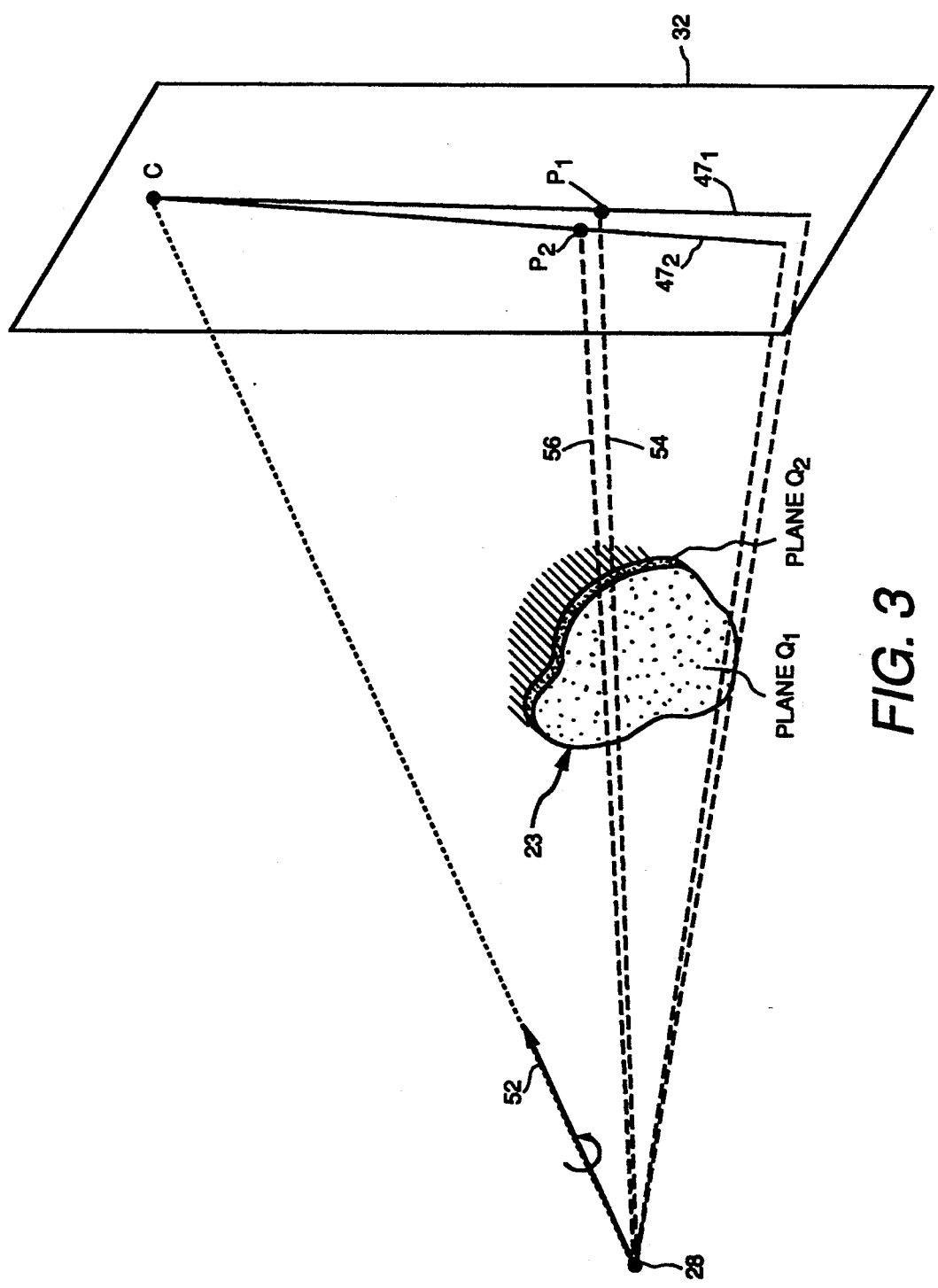
FIG. 3 depicts further details for obtaining Radon data corresponding to a pair of lines of integration similar to the line of integration illustrated in FIG. 2.

FIG. 3 illustrates a pair of lines of integration $47_1$ and $47_2$ which share a rotation center C for obtaining Radon data. Let us consider a plane $Q_2$ which is relatively close to plane $Q_1$ (analogous to plane 46 in FIG. 2). Plane $Q_2$ is obtained by rotating plane $Q_1$ by a suitable angle about a rotation axis 52 situated on plane $Q_1$ and passing through a given source scan position. Selection of the actual rotation angle is a compromise between accuracy and signal-to-noise ratio for a particular system implementation. It should be appreciated that a point $P_1$ situated on line of integration $47_1$ represents the integrated density of x-ray imaging energy along a path 54 which lies on plane $Q_1$ and extends from the x-ray source 28 to point $P_1$. Similarly, the point $P_2$ situated on line of integration $47_2$ represents the integrated density of x-ray imaging energy along path 56 which lies on plane $Q_2$ and extends from the x-ray source 28 to point $P_2$. Measuring the difference between the respective detected values on points $P_1$ and $P_2$, respectively, allows for measuring the difference between the integrated densities along paths 54 and 56 situated on the integration planes $Q_1$ and $Q_2$, respectively.

Figure 4A:
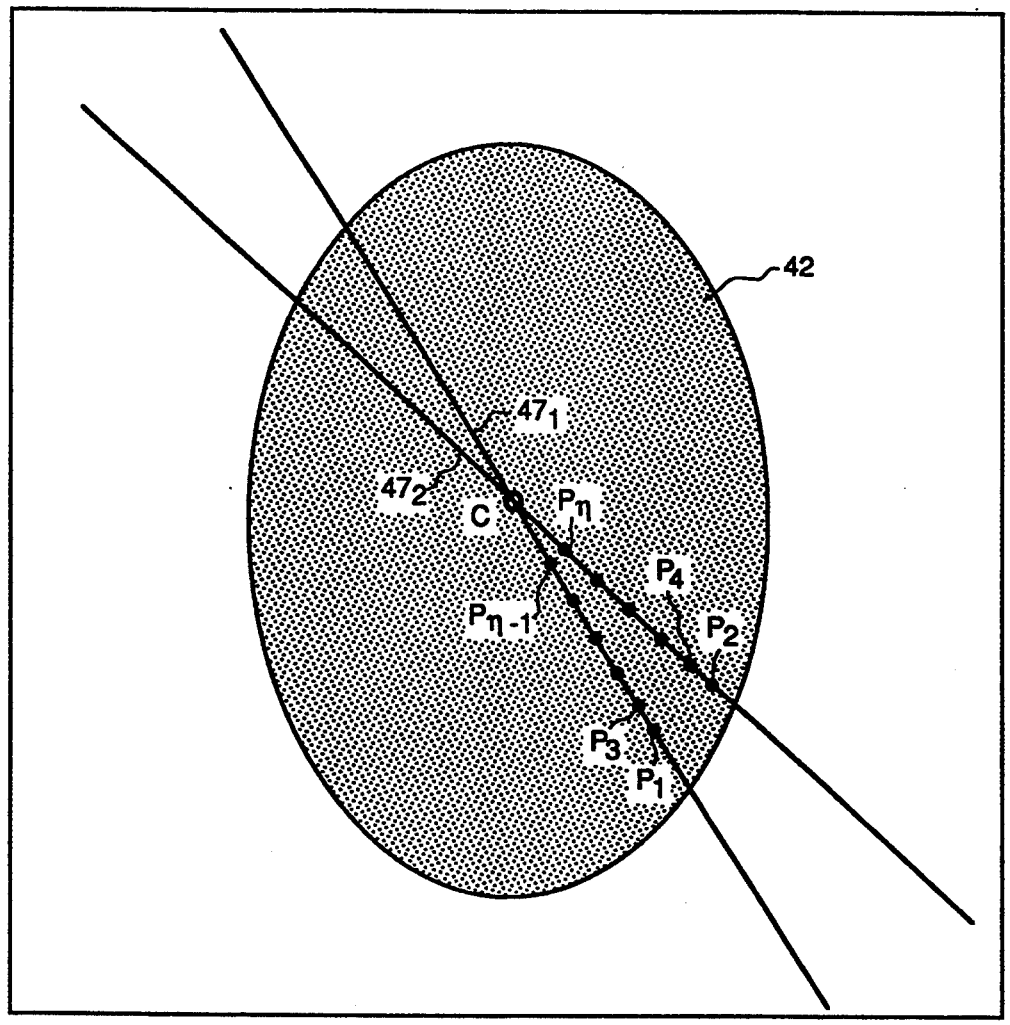
FIGS. 4a and 4b depict exemplary points situated along a line of integration pair and further illustrate details of how such points are mapped onto one another for obtaining Radon data.

As best appreciated in FIG. 4a, the difference between respective points (such as between exemplary corresponding points $P_1$ and $P_2$; $P_3$ and $P_4$; and $P_{n-1}$ and $P_n$) can be suitably weighted and integrated along the entire length of line of integration pair $47_1$ and $47_2$.

In essence, such weighted integration allows to compute the overall difference between the integrated densities corresponding to the entire integration planes $Q_1$ and $Q_2$ shown in FIG. 3. This last computed overall difference can be conveniently related to the derivative of the Radon transform of the portion of interest to be imaged inasmuch as the Radon transform of the portion of interest at a given point is the integrated density of the portion of interest over a plane passing through such point (as discussed in the context of FIG. 3 with reference to the exemplary points $P_1$ and $P_2$ shown therein). Thus, implicit in the Radon derivative computation is identifying a rotation center shared by at least a pair of the lines of integration such as line of integration pair $47_1$ and $47_2$, for example. The rotation center is selected for suitably mapping respective ones of the corresponding points situated along the line of integration pair. Those skilled in the art will appreciate that suitable selection of the rotation center provides a one-to-one onto mapping relationship to respective ones of the corresponding points situated along each line of integration pair. As used herein a one-to-one onto mapping refers to mapping corresponding points on the line of integration pair such that each point in one of the lines of integration maps with only one corresponding point of the other line of the line of integration pair. In particular, for the Radon derivative to be effectively computed, the one-to-one onto mapping must satisfy a criterion wherein the values on each of the corresponding points (e.g., $P_1$ and $P_2$ used in calculating the weighted integration must actually represent the integrated density of x-ray imaging energy along each respective path (e.g., paths 54 and 56 in FIG. 3) associated with any given corresponding points (e.g., $P_1$ and $P_2$). For example, point $P_1$ maps only with a corresponding point $P_2$, point $P_3$ maps only with a corresponding point $P_4$ and so on. As can be appreciated in FIG. 4a, the one-to-one onto mapping relationship is satisfied in conventional cone beam imaging which does not use the masking operation used for region of interest imaging.

Figure 4B:
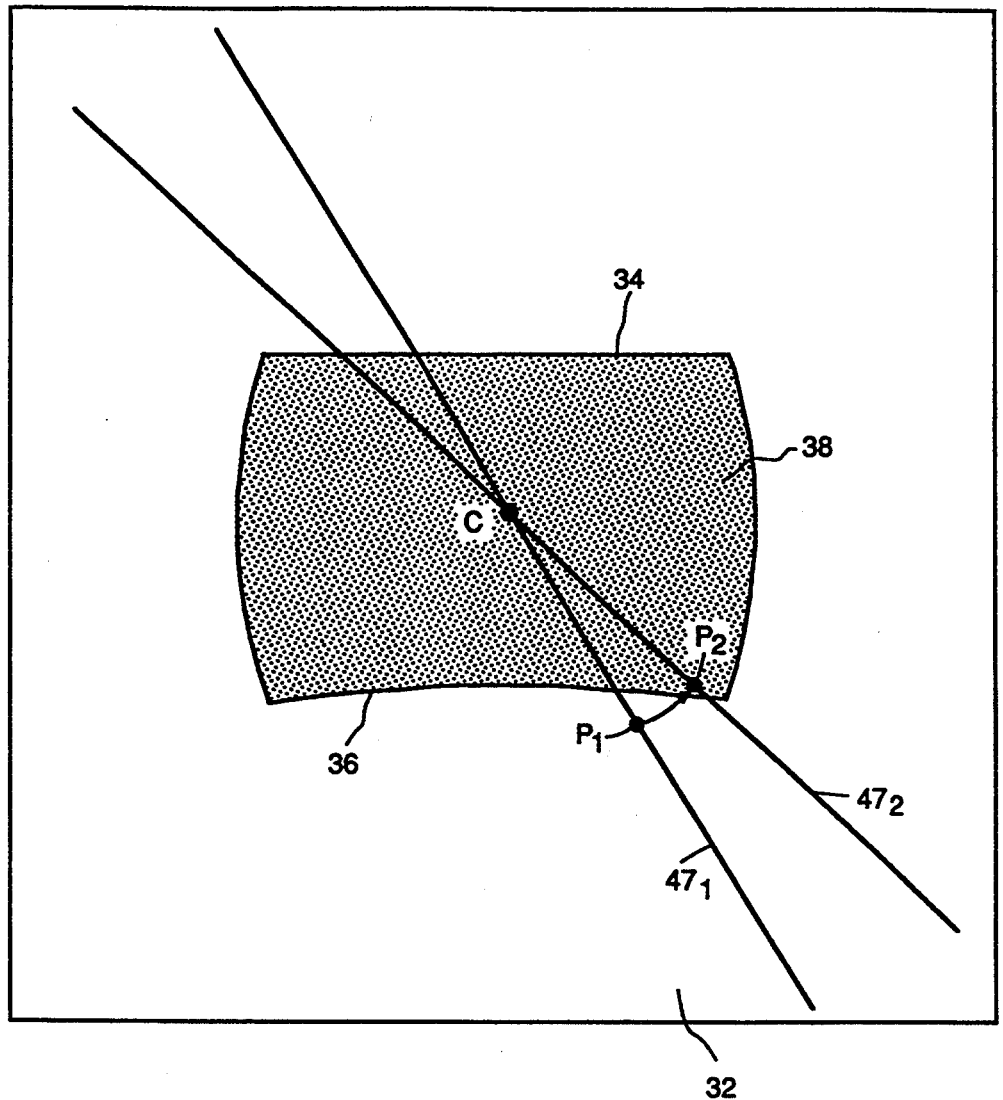

FIG. 4b illustrates that after performing the masking operation described in the context of FIGS. 1a and 1b, the one-to-one onto mapping relationship with the foregoing criterion no longer holds. For instance, whenever the line of integration pair $47_1$ and $47_2$ intersects a predetermined boundary of the identified cone beam masked region 38, such as the lower scan path projection 36 (i.e., the parabolic curve boundary), in general there will be points such as exemplary points $P_1$ and $P_2$ which do not map within the identified region 38, that is, there are points $P_1$ and $P_2$ which do not map onto each other upon rotation about rotation center C and which provide respective values that actually represent the integrated density of x-ray imaging energy along a path such as paths 54 and 56 in FIG. 3. Consequently there are points located on one of the lines of the line of integration pair which are situated inside region 38 which are mapped upon rotation about rotation center C onto points on the other line of the line of integration pair which are situated outside region 38, such as is the case for exemplary points $P_1$ and $P_2$ illustrated in FIG. 4b. Since point $P_1$ is outside region 38, the image value corresponding thereto is set to zero in the masking operation. Therefore, in computing the weighted integral corresponding to the line of integration pair $47_1$ and $47_2$, there is no contribution from point $P_1$ to balance the contribution from point $P_2$. The end result is that the computed weighted integral includes certain errors since such weighted integral not only measures the spatial change of the integrated density for the integration plane under rotation; but the computed weighted integral will also reflect the effect of the predetermined boundary for the identified cone beam masked region 38. The effects of the errors induced by such predetermined boundary generally produce noticeable artifacts in the image of the portion of interest. This source of errors is referred herein as boundary-induced artifacts. Specifically, the boundary-induced artifacts occur only due to parabolic curve boundary 36 but not due to the straight line boundary 34. The reason being that whereas the actual image value outside boundary 36 is in general non-zero, the actual image value outside boundary 34 is strictly zero.

Figure 5:
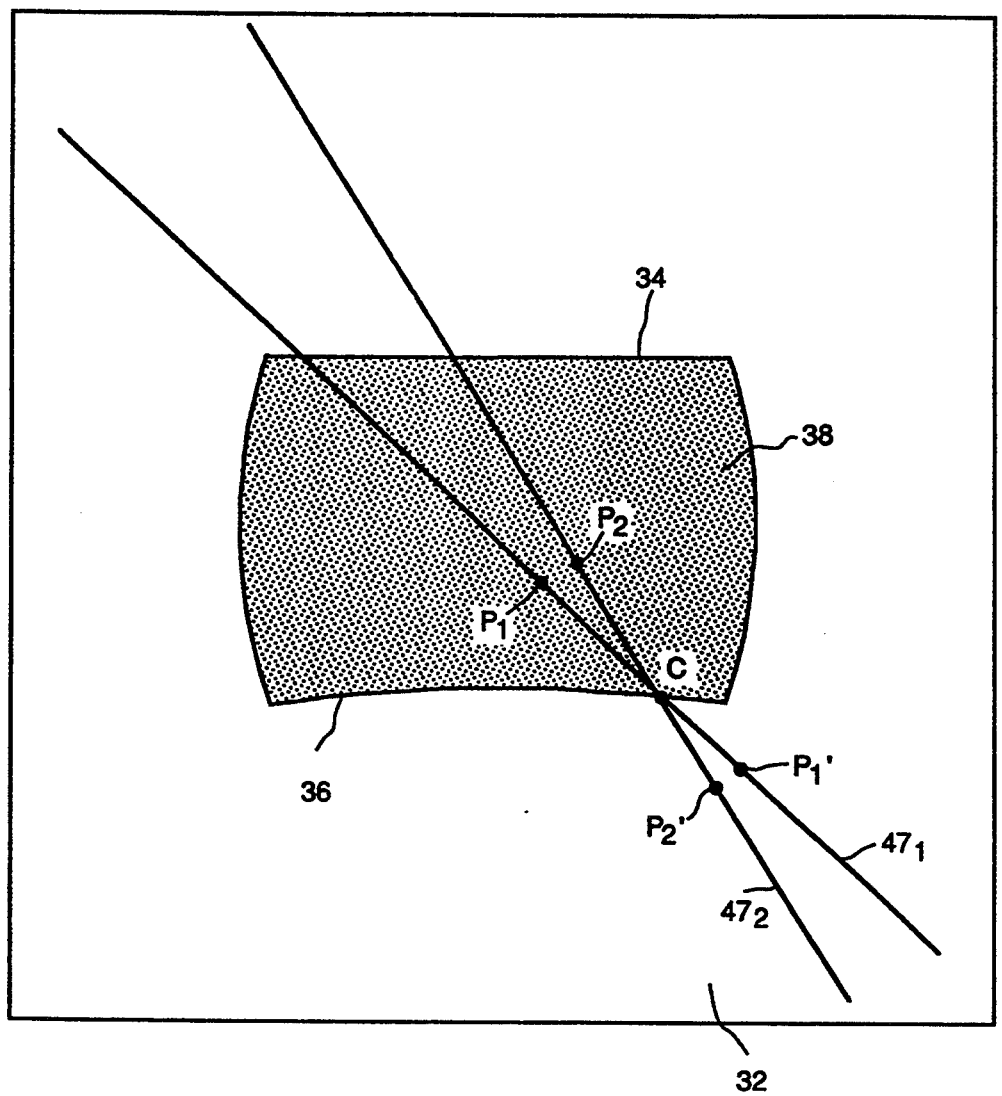
FIG. 5 depicts an exemplary rotation center situated on the lower scan path projection in accordance with an embodiment of the present invention.

As will be appreciated in the exemplary embodiment shown in FIG. 5, the present invention substantially eliminates boundary-induced artifacts by an appropriate choice of the location for the rotation center C. For the purpose of illustration, the following description assumes that the lower scan path projection is the parabolic curve boundary. However, it is to be understood that such illustration is merely exemplary being that such parabolic lower scan path projection is obtained from source positions, such as position A in FIG. 2, at the upper scan path. In other situations the upper scan path projection can easily become the parabolic curve boundary, and that is the case when the upper scan path projection is obtained from source positions, such as position B in FIG. 2, at the lower scan path. Keeping in mind the foregoing, boundary-induced artifacts occur by way of example when the line of integration pair intersects the lower scan path projection 36, i.e., the parabolic curve obtained from source positions at the upper scan path. If the line of integration pair $47_1$ and $47_2$ does not intersect the parabolic boundary, then the rotation center C can be located anywhere on detector 32, for example. In a more general case since the rotation center is merely a conceptual representation and not a physical rotation center such rotation center is not limited to being located on detector 32 and can be selected to be located anywhere on the line of integration so long as the mapping, within the identified cone beam masked region 38, of corresponding points on the line of integration pair is maintained. Conversely, if the line of integration pair $47_1$ and $47_2$ intersects the parabolic boundary, then, in accordance with the exemplary embodiment shown in FIG. 5, identify such intersection as the rotation center C, that is, the rotation center is identified to be located on the surface array detector along the lower scan path projection for each line of integration pair which intersects the lower scan path projection. More generally those skilled in the art will appreciate that the rotation center can be located on the surface array detector along a predetermined one of the upper and lower scan path projections such that the one scan path projection, i.e., the parabolic curve boundary, whereon the rotation center is located is obtained from source positions located at the respective one of the upper and lower scan paths which forms the other of the upper and lower scan path projections, i.e., the straight line boundary. In the embodiment illustrated in FIG. 5, the predetermined one scan path projection along which the rotation center is located is the lower scan path projection, i.e., the parabolic curve boundary obtained from source positions located at the upper scan path which is the path that in this case forms the other scan path projection, i.e., the straight line boundary.

Similarly, in other situations wherein the upper scan path projection is the parabolic curve boundary, then the predetermined one scan path projection along which the rotation center can be located is the upper scan path projection obtained from source positions located at the lower scan path which is the scan path that in this case forms the other scan path projection, i.e., the straight line boundary. The expression "other scan path projection" in each case simply refers to the scan path projection not affected by the boundary-induced artifacts, i.e., the straight line boundary.

As can be seen from FIG. 5, the rotation center C divides each of the lines of the line of integration pair $47_1$ and $47_2$ into respective segments which either lie inside the cone beam masked region 38 or lie outside region 38. For example, in making a rotation from line of integration $47_1$ to line of integration $47_2$, all the points on the segment of line of integration $47_1$ outside region 38 are mapped to the points on the segment of line of integration $47_2$ outside region 38. This is represented by points $P'_1$ and $P'_2$ in FIG. 5. Conversely all the points on the segment of line of integration $47_1$ inside region 38 are mapped to the points on the segment of line of integration $47_2$ inside the mask. This is represented by points $P_1$ and $P_2$ in FIG. 5. Since none of the points on the segment of line of integration $47_1$ inside region 38 is mapped to the segment of line of integration $47_2$ outside region 38, and since none of the points on the segment of line of integration $47_1$ outside region 38 are mapped to the segment on line of integration $47_2$ inside region 38, then the errors which cause the boundary-induced artifacts are therefore effectively eliminated. Cone beam projection data can thus be conveniently acquired at detector 32 for a plurality of scan positions along the scan trajectory. Further by retaining cone beam projection data acquired in the identified cone beam masked region 38 insures that subsequent processing of such retained data results in reconstructing a 3D image of the portion of the object which is substantially free of boundary-induced artifacts. The image reconstruction being implemented, for example, by using the inverse Radon transformation.

Techniques for allowing computation of Radon data from cone beam projection data can be performed in known fashion and need not be described in detail. Briefly, most image reconstruction procedures in x-ray CT are based on the Radon inversion process, in which the image of an object is reconstructed from the totality of the Radon transform of the object. The Radon transform of a 3D object consists of planar integrals. The cone beam projection data, however, is not directly compatible with image reconstruction through inverse Radon transformation, which requires the use of planar integrals of the object as input. Consequently, image reconstruction by inversion from cone beam scanning data generally comprises two steps. A first step is to convert the cone beam data to planar integrals. A second step is then to perform an inverse Radon transform on the planar integrals to obtain the image.

The first step is described by the present inventor's U.S. Pat. No. 5,257,183, issued Oct. 26, 1993, entitled "METHOD AND APPARATUS FOR CONVERTING CONE BEAM X-RAY PROJECTION DATA TO PLANAR INTEGRALS AND RECONSTRUCTING A THREE-DIMENSIONAL COMPUTERIZED TOMOGRAPHY (CT) IMAGE OF AN OBJECT", assigned to the assignee of the present application and hereby incorporated by reference. A technique for performing an inverse Radon transform on planar integrals to obtain an image is described in the present inventor's prior U.S. patent application Ser. No. 07/631,818, filed Dec. 21, 1990, now abandoned for FWC Ser. No. 08/174,170 entitled "PARALLEL PROCESSING METHOD AND APPARATUS FOR RECONSTRUCTING A THREE-DIMENSIONAL COMPUTERIZED TOMOGRAPHY (CT) IMAGE OF AN OBJECT FROM CONE BEAM PROJECTION DATA OR FROM PLANAR INTEGRALS", assigned to the assignee of the present application, and hereby incorporated by reference. Thus, the foregoing incorporated by reference patent and prior U.S. patent applications describe techniques which may be used for three-dimensional image reconstruction by Radon inversion from cone beam projection data.

Figure 6:
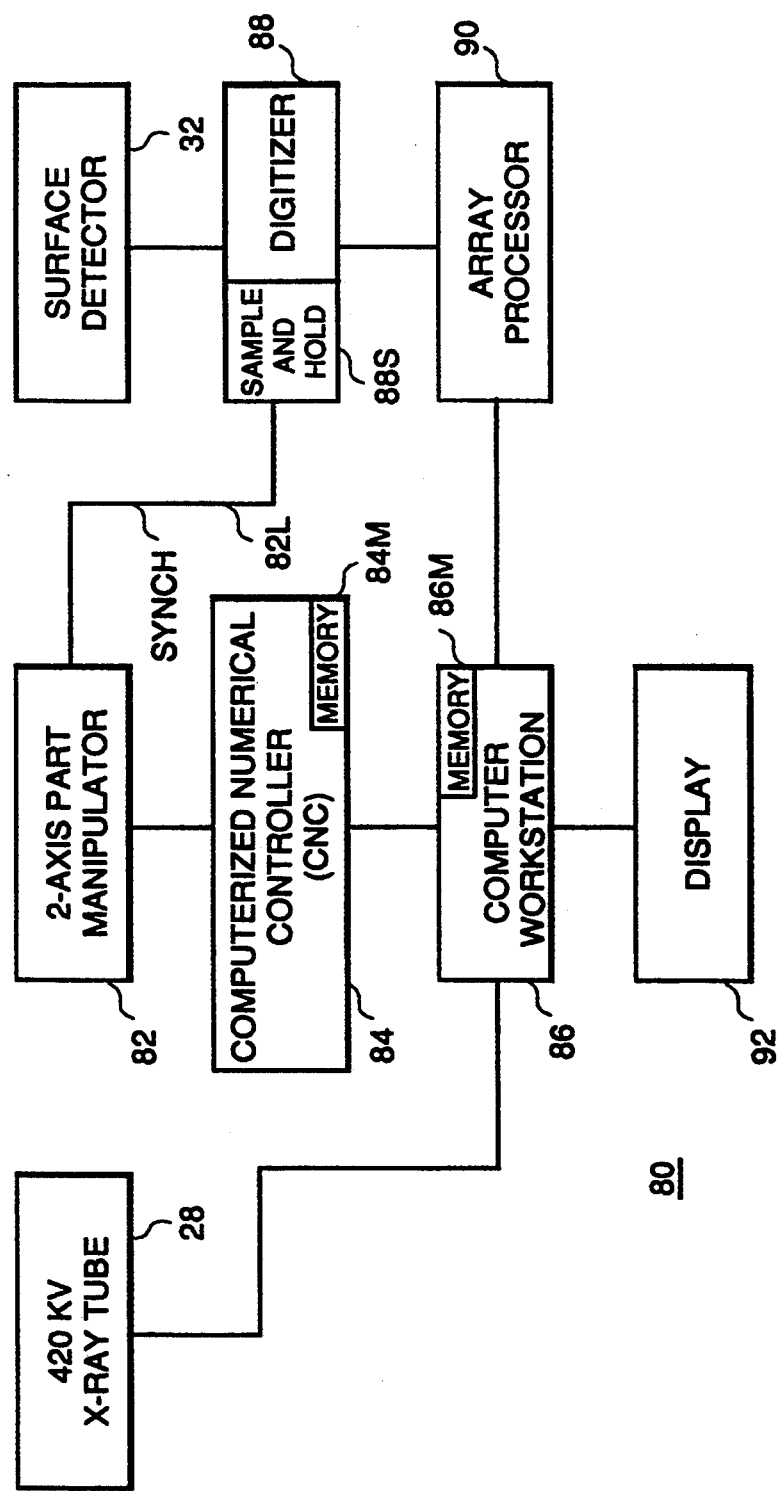
FIG. 6 is a simplified block diagram illustrating components of the system of the present invention.

Turning now to FIG. 6, a system 80 according to the present invention will be discussed. The system includes the cone beam radiation source 28 and surface array detector 32. Although the source 28 is shown as an x-ray tube, the cone beam radiation source 28 could alternatively provide neutrons, positrons, or other forms of radiation or electromagnetic energy from a point source. Alternatively, other forms of imaging energy might be used.

A manipulator 82, which may be a two-axis part manipulator, is an example of a scanning device used to provide the relative scanning movement between the portion (not shown in FIG. 6) which is to be imaged and the source 28. Although the manipulator 82 is designed to move the object, the manipulator 82 might alternatively move the source 28.

The manipulator 82 is controlled by a known computerized numerical controller (CNC) 84, which may, for example, be of a type made by Aerotech. The controller 84 may include a memory 84M having suitable data defining the scan trajectory path in known fashion. Alternatively, and also using well known techniques, a memory 86M of a computer work station 86, which is connected to the controller 84, may have the data which defines movements of the manipulator 82 and therefore defines the trajectory of the type previously discussed with respect to FIGS. 1a and 2 of the present application. The computer work station 86 may be a work station made by Sun, although other computer work stations and possibly even personal computers might be used in place of the work station. The computer work station controls the other components of the system 80 in known fashion. Further, the computer work station can conveniently provide stored within memory 86M a program having a module for identifying the cone beam masked region 38 discussed in the context in FIGS. 1a, 1b, 2, 4b and 5. Memory 86M or memory 84M can provide convenient means for retaining cone beam projection data acquired within the masked region.

Connected to the surface array detector 32 is a digitizer 88 which operates in known fashion to convert analog signals from the array detector into digital signals representative of the image of the portion undergoing inspection. The digitizer 88 may include sample and hold circuits 88S operating in response to a synch signal on line 82L in known fashion. Thus, digitizer 88 provides suitable means for acquiring cone beam projection data at predetermined points situated along respective lines of integration traversing the identified region 38 on the surface detector array. Further, the computer work station can conveniently provide stored within memory 86M a program having a module for identifying the rotation center shared by at least a pair of the lines of integration as described in the context of FIG. 5. The rotation center being selected to map within the identified region 38 respective ones of the points situated along the line of integration pair.

The digitized values corresponding to the detected cone beam radiation, that is, cone beam projection data from the detector elements, i.e., pixel detectors within detector 32, are supplied from the digitizer 88 to a data array processor 90. The array processor 90, which may be of a known commercially available type such as a Meiko M40, provides the necessary signal processing for the signals coming from the digitizer 88. The array processor 90 may perform the necessary image reconstruction and processing such that a display might be connected directly to the array processor to display the images from the CT scan. However, in the arrangement shown in FIG. 6, the image data from array processor 90 is supplied to computer work station 86 and the computer work station 86 in turn supplies the data, with or without further processing, to a display 92 which displays the CT images. The computer 86 or, more preferably, array processor 90 reconstructs an image from a complete data set generated from combining cone beam data corresponding to respective subportions of the portion to be imaged such as suitable upper and lower subportions, for example. Thus, either computer workstation 86 or array processor 90 provide suitable means for processing the retained cone beam data combined to generate the complete data set which can be exactly reconstructed into an image of the portion of interest.

Upon suitable operation of the manipulator 82, the system 80 of FIG. 6 may be used to realize techniques described in the context of FIGS. 1a and 2. That is, the manipulator 82 may simply move the object (not shown in FIG. 6) in a scanning movement relative to source 28 along the scan trajectory having upper or lower scan paths. It will be appreciated that the scanning movement along the scanning trajectory can be either stepwise or continuous scan depending on the particular implementation.

Stored within memory 84M or memory 86M would be a program having a module which controls manipulator 82 and/or possibly a second manipulator (not shown) in order to position the object, source, and array detector in suitable scanning positions. Another module of the program, most likely stored in memory 86M, would organize the cone beam data corresponding to each of the respective subportions of the portion to be imaged. The program would further include a module for combining the cone beam data of each subportion to provide the complete data set corresponding to the portion of interest to be imaged.

Although various specific constructions have been given for the present invention, it is to be understood that these are for illustrative purposes only. Various modifications and adaptations will be readily apparent to those of skill in the art. For example, although the present invention has been described with reference to a scan trajectory having upper and lower circular scan paths, other alternatives are possible. For example, a helical path which encloses the portion to be imaged may be conveniently defined as the scan trajectory. In this case, the masked region can be suitably identified to retain the cone beam data being generated using such helical path. In view of these and other modifications, the scope of the present invention should be determined by reference to the claims appended hereto.

What is claimed:

1. A method of processing cone beam projection data for reconstructing substantially free of boundary-induced artifacts a three-dimensional (3D) image of at least a portion of an object using an inverse Radon transformation, said method comprising the steps of:
providing a mutually spaced cone beam source and a surface array detector in fixed relationship to one another;
using said source for irradiating at least said portion of said object positioned between said source and said detector within a field of view of said source;
moving both said source and detector relative to said object for scanning about said portion along a scan trajectory enclosing upper and lower extents of said portion by respective upper and lower scan paths joined therebetween by a predetermined connecting path;
identifying on said surface array detector a region selected to match a cone beam projection of said object bounded between respective similar projections of said upper and lower scan paths;
acquiring cone beam projection data at predetermined points situated along respective lines of integration traversing said identified region on said surface array detector;
identifying a rotation center shared by at least a pair of said lines of integration wherein said rotation center is selected for mapping within said identified region respective ones of said points situated along said line of integration pair;
retaining cone beam projection data acquired within said identified region; and
processing said retained data to reconstruct substantially free of boundary-induced artifacts a 3D image of said portion using said inverse Radon transformation.

2. A method in accordance with claim 1 wherein said rotation center is located on said surface array detector along a predetermined one of said upper and lower scan path projections such that said one scan path projection whereon said rotation center is located is obtained from source positions located at the respective one of said upper and lower scan paths forming the other of said upper and lower scan path projections.

3. A method in accordance with claim 2 wherein said rotation center is located on said surface array detector along said lower scan path projection for each said line of integration pair intersecting said lower scan path projection.

4. A method in accordance with claim 3 wherein said source positions are located at said upper scan path.

5. A method in accordance with claim 2 wherein said rotation center is located on said surface array detector along said upper scan path projection for each said line of integration pair intersecting said upper scan path projection.

6. A method in accordance with claim 5 wherein said source positions are located at said lower scan path.

7. A method in accordance with claim 1 wherein said mapping within said identified region provides a one-to-one onto mapping relationship to respective ones of said points situated along each said line of integration pair.

8. A method in accordance with claim 7 further comprising displaying the reconstructed 3D image of said portion of the object.

9. A method in accordance with claim 1 wherein said cone beam source irradiates x-ray energy.

10. A system for processing cone beam projection data to reconstruct substantially free of boundary-induced artifacts a three-dimensional (3D) image of a portion of an object, said system comprising:
a cone beam source for irradiating at least said portion of said object;
a surface array detector positioned in fixed relationship with reference to said source to receive radiation from said source;
a scanning device causing relative motion of said source and object such that said source moves along a scan trajectory relative to said portion of said object, said device including means for scanning along upper and lower scan paths of said trajectory respectively enclosing upper and lower extents of said portion of said object and a connecting scan path therebetween;
means for identifying a region on said surface array detector selected to match a cone beam projection of said object bounded between respective similar projections of said upper and lower scan paths;
means for acquiring cone beam projection data at predetermined points situated along respective lines of integration traversing said identified region on said surface array detector;
means for identifying a rotation center shared by at least a pair of said lines of integration wherein said rotation center is selected to map within said identified region respective ones of said points situated along said line of integration pair;
means for retaining cone beam projection data acquired within said identified region; and
means for processing said retained data into a 3D image of said portion by a Radon inverse transformation, said image being substantially free of boundary-induced artifacts.

11. A system in accordance with claim 10 wherein said rotation center is located on said surface array detector along a predetermined one of said upper and lower scan path projections such that said one scan path projection whereon said rotation center is located is obtained from source positions located at the respective one of said upper and lower scan paths forming the other of said upper and lower scan path projections.

12. A system in accordance with claim 11 wherein said rotation center is located on said surface array detector along said lower scan path projection for each said line of integration pair intersecting said lower scan path projection.

13. A system in accordance with claim 12 wherein said source positions are located at said upper scan path.

14. A system in accordance with claim 11 wherein said rotation center is located on said surface array detector along said upper scan path projection for each said line of integration pair intersecting said upper scan path projection.

15. A system in accordance with claim 14 wherein said source positions are located at said lower scan path.

16. A system in accordance with claim 10 wherein said rotation center identifying means is adapted to map respective ones of said points situated along each said line of integration pair in a one-to-one onto mapping relationship.

17. A system in accordance with claim 16 further comprising a display device connected to said processing means to display the reconstructed 3D image of said portion of the object.

18. A system in accordance with claim 10 wherein said cone beam source is an x-ray energy cone beam source.

* * * * *